United States Patent [19]

Barnette

[11] 4,434,316

[45] Feb. 28, 1984

[54] SEPARATION OF ALKENES FROM ALKADIENES

[75] Inventor: Willie J. Barnette, Orange, Tex.

[73] Assignee: E. I. Du Pont de Nemours & Co., Wilmington, Del.

[21] Appl. No.: 478,997

[22] Filed: Mar. 25, 1983

[51] Int. Cl.³ .............................................. C07C 7/00
[52] U.S. Cl. .................................................. 585/833
[58] Field of Search ...................... 585/833; 260/465.3

[56] References Cited

U.S. PATENT DOCUMENTS 3,496,210 2/1970 Drinkard et al. .................... 260/465
3,496,215 2/1970 Drinkard et al. ................. 260/465.8
3,766,237 10/1973 Chia ................................. 260/465.3
3,775,461 11/1973 Drinkard ......................... 260/465.3
3,778,462 12/1973 Taylor ............................. 260/465.3
3,798,256 3/1974 King et al. ...................... 260/465.3
3,850,973 11/1974 Seidel et al. ...................... 260/464
3,903,120 9/1983 Shook, Jr. et al. .............. 260/465.3
3,920,721 11/1975 Gosser ............................. 260/465.3

Primary Examiner—Delbert E. Gantz
Assistant Examiner—Cynthia A. Prezlock

[57] ABSTRACT

Process for separating alkenes, e.g., butene, from alkadienes, e.g., butadiene by preferentially hydrocyanating the diene and thereafter recovering the unreacted alkenes.

6 Claims, 1 Drawing Figure

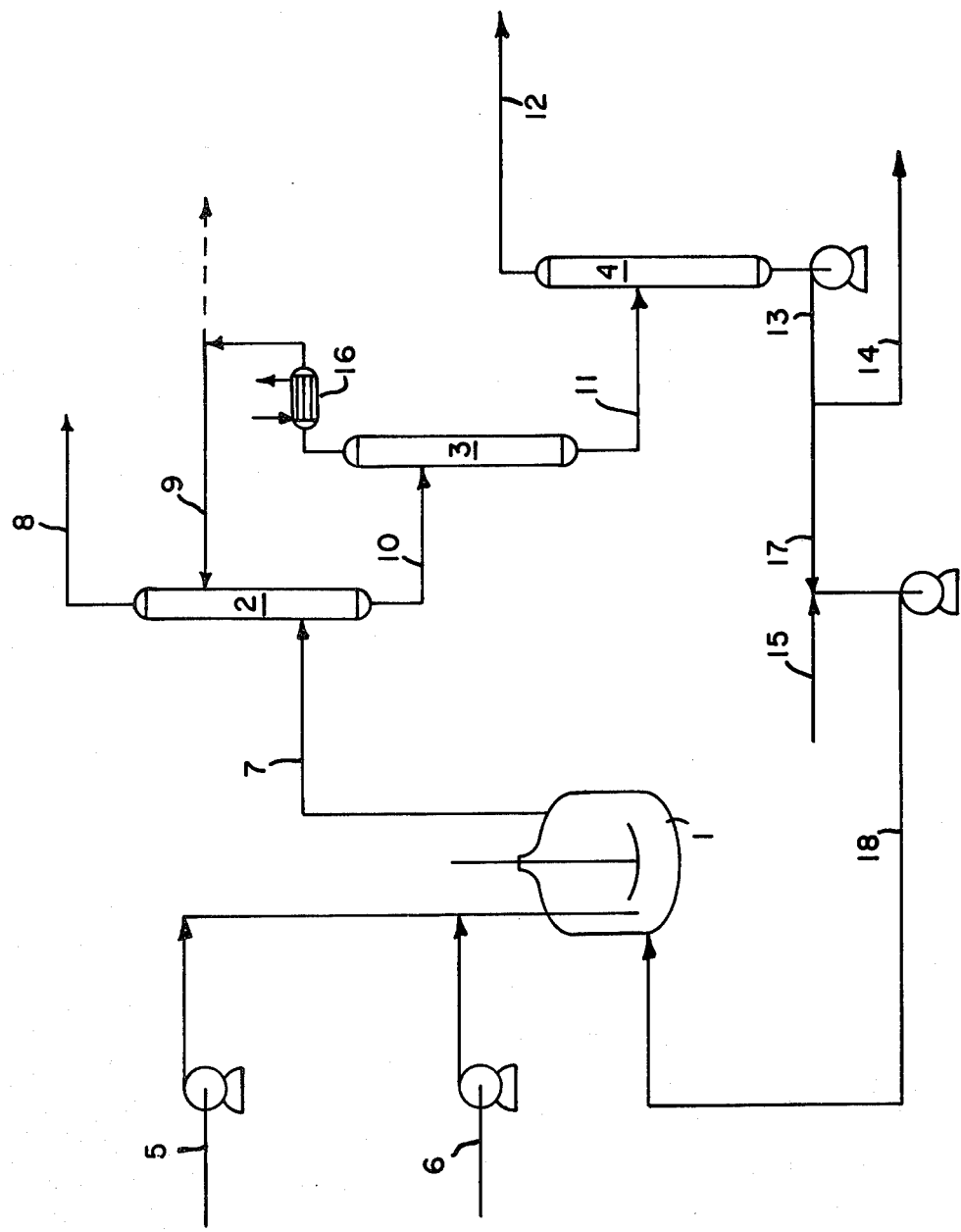

SEPARATION OF ALKENES FROM ALKADIENES

BACKGROUND OF THE INVENTION

1. Field of the Invention

The present process is directed to the separation of alkenes, e.g., butene from polyunsaturated hydrocarbons such as alkadienes, e.g., butadiene by preferentially hydrocyanating alkadienes in mixture with alkenes to their corresponding nitriles and thereafter recovering the unreacted alkenes.

2. Description of the Prior Art

The hydrocyanation process employed in the separation process of the present invention is well defined. In commercial application it includes a two-step reaction, e.g., the sequential addition of hydrogen cyanide to a diolefin such as butadiene to first produce 3- and/or 4-pentenenitrile and then to produce adiponitrile as the second step. The present invention employs a reaction similar to this first step in the hydrocyanation process. A full description of this first step is contained in U.S. Pat. No. 3,496,215 issued on Feb. 17, 1970 and includes a description of the general type of catalyst which is employed and the temperatures and pressures at which the hydrocyanation should be conducted. Additional discussion of the first step of the hydrocyanation reaction using a $\pi$-allyl nickel complex catalyst is found in U.S. Pat. No. 3,850,973 issued on Nov. 26, 1974.

A process of hydrocyanating terminal alkynes is disclosed in U.S. Pat. No. 3,496,210 issued on Feb. 17, 1970. The disclosures of the foregoing references are incorporated herein by this reference.

U.S. Pat. No. 3,496,215 suggests that the addition of HCN to a double bond can be accomplished with both diolefins and monoolefins (Column 1, lines 45-60). Applicant has discovered that under the conditions herein disclosed hydrogen cyanide can be preferentially reacted with a diolefin contained in a mixture comprising monoolefins which have physical properties close to the diolefin and thereby producing an unsaturated nitrile from the diolefin from which the monoolefin can be readily separated, e.g., by distillation.

SUMMARY OF THE INVENTION

The present invention is a process for separating alkenes, e.g., butene from mixtures of alkenes and alkadienes, e.g., butadiene wherein the separation is achieved by preferentially reacting hydrogen cyanide with the diene by contacting the mixture with hydrogen cyanide under hydrocyanation conditions preferably in the presence of a zerovalent nickel catalyst.

The process is conducted at a temperature in the range 40°- ⓡ° C. and preferably 60°-150° C. at a pressure in the range 0.1-5 MPa and preferably 1-3 MPa.

DETAILED DESCRIPTION OF THE INVENTION

The physical properties of alkenes having 2-5 carbon atoms and alkadienes having 3-8 carbon atoms are sufficiently close as to render separation under commercially attractive conditions quite difficult. In commercial processes which are directed to the preparation of dinitriles, it is necessary to separate alkenes which do not form dinitriles from the alkadienes. Previous practice affected the alkene/alkadiene separation by extractive distillation using solvents such as furfural, acetonitrile, dimethylacetamide, dimethylformamide, n-methylpyrrolidone, or other costly solvents. High energy consumption, complicated equipment, some loss of BD by polymerization and buildup of acetylenic materials are disadvantages of this extractive distillation. Applicant has discovered that when a mixture of alkenes and alkadiene is exposed to certain hydrocyanation conditions, the alkadienes will preferentially hydrocyanate to mononitriles which because their physical properties now differ from the alkene can be readily separated therefrom.

Alkenes which can be separated by the present invention includes those selected from the groups having 2-5 carbon atoms, e.g., ethylene, propylene, butenes and pentenes. Alkadienes which are readily separated from the foregoing alkenes include alkadienes selected from the groups having 3-8 carbon atoms, e.g., propadiene, butadiene, pentadiene, hexadiene and octadiene. The presence of acetylenic and ethylenic-acetylenic hydrocarbons will not adversely affect the separation of the alkenes.

Preferably a catalyst described by the formula $NiL_4$ wherein L is $P(OAr)_3$ and Ar is an alkyl or aryl group having from 6-10 and preferably 6-8 carbon atoms is employed to assist in the hydrocyanation. It is also preferred to conduct the reaction in the presence of an excess of ligand [(L) in the above formula] such that the excess ligand to nickel ratio is usually in the range 2-26 and preferably in the range 10-18.

The art discloses that the activity of the nickel catalyst as described hereinabove may be improved by the use of certain promoters such as alkali-earth metal halides and certain triaryl boranes. It is preferred to conduct the present process in the absence of promoters.

It is desirable to conduct the reaction in the liquid phase. This does not require that any additional solvent be used since the aforementioned ligand can serve as a solvent, however, the reaction can be conducted using an inert organic solvent which is a liquid at the reaction temperature and inert towards the reactants and the catalyst. Generally, solvents such as benzene, cyclohexane, acetonitrile, 3-pentenenitrile and benzonitrile are suitable.

The reaction is maintained in the liquid state by the proper selection of temperature and/or pressure. Generally, pressures in the range of 0.1-5 MPa and preferably 1-3 MPa are most advantageously employed. Temperatures in the range of 40°-200° C. and preferably in the range of 60°-150° C. are employed.

The reaction can be conducted batchwise but it is preferred to conduct the reaction continuously since the unreacted olefin is readily separated from the pentenenitrile reaction product by simple flash distillation which can be accomplished by reducing the pressure of the reaction product exiting the reactor. The holdup time during which the reaction is conducted is not critical but usually is in the range of 5-300 minutes and preferably 10-40 minutes.

The following Example is presented to illustrate but not to restrict the present invention. Parts and percentages are by weight unless otherwise noted.

EXAMPLE

A schematic diagram of the apparatus employed in this example is shown in the FIGURE. The main equipment includes pressure reactor 1 and distillation columns 2, 3, and 4. All equipment is designed to be operated under pressure with suitable pumps and controls provided. The alkene-alkadiene mixture is introduced into reactor 1 via line 5 along with uninhibited liquid HCN via line 6 after both streams have been pressurized. During normal operation reactor 1 is maintained at internal pressure of approximately 1.5 MPa and a temperature of 107° C. with essentially no vapor space. The effluent from reactor 1 (line 7) is directed to flash distillation column 2 which column is maintained at a pressure of approximately 0.44 MPa and at a base temperature of about 135° C. Unreacted alkenes are flash distilled and are removed as heads (line 8).

The tails from flash distillation column 2 (line 10) are directed to column 3 which is operated at a pressure 0.1 MPa and a base temperature of about 136° C. In order to reduce the number of streams in this Example, heads from column 3 are condensed in condenser 16, repressurized and introduced into column 2 via line 9 to permit their removal along with the monoolefin. Streams 8 and 9 can be combined or processed separately. The tails from column 3 which comprise the mononitrile, catalyst, and excess ligand are directed to mononitrile recovery column 4 where the crude mononitrile is recovered overhead and directed to purification (line 12). This column is operated at a pressure of 0.015 MPa and a temperature of 125° C. A portion (line 14) of the tails from column 4 (line 13) is removed and the remainder (line 17) combined with fresh catalyst via line 15 then recycled to reactor 1 via line 18. Catalyst solution is prepared by reacting a mixture containing 70% tritolyl (mixed m,p-tolyl) phosphite, 10% pentenenitriles (mostly 3-, 4-pentenenitriles), 8% dinitriles (mostly adiponitrile) and 3% nickel powder to which mixture had been added 100 ppm chloride catalyst as phosphorus trichloride. The mixture is heated for 16 hours at 80° C., cooled and filtered to yield a solution shown in Table 1, stream 15. The solution is charged to reactor 1 and columns 2, 3 and 4 after they are purged with $N_2$ to remove all traces of oxygen. The flow rate of recycled catalyst to the reactor is established at 5.74 ppH. The reactor runs liquid filled and the effluent flow out of the reactor is adjusted to maintain a pressure of 1.5 MPa. Base level in each of the column is maintained by adjusting effluent flow. After establishing catalyst flow, the temperatures of the reactor 1 and columns 2, 3 and 4 are adjusted to 107° C., 135° C., 136° C. and 125° C. respectively. The flow rate of mixed alkenes and alkadienes through line 5 is begun at a rate of 2.62 ppH and boilup and pressure is established in columns 2 and 3. Uninhibited HCN is introduced to the reactor through line 6 at a flow rate of 0.48 ppH. Boilup and pressure in column 4 is established with the mononitriles produced leaving via line 12. Makeup and purge catalyst are adjusted at flow rates of 0.275 and 0.24 ppH which maintains nickel concentration in reactor 1 at about 0.5%.

After steady state operation is achieved following the above startup procedure, the streams listed in the Table are analyzed and the results reported therein.

TABLE I

| | Stream No. | | | | | | |
|---|---|---|---|---|---|---|---|
| | 5 | 6 | 8 | 11 | 12 | 14 | 15 |
| Flow (pph) | 2.62 | 0.48 | 1.75 | 7.09 | 1.39 | 0.24 | 0.275 |
| Components (Wt %) | | | | | | | |
| Butadiene | 43.0 | | 12.4 | 0.05 | | | |
| Butane | 1.3 | | 1.9 | — | | | |
| Butene | 55.1 | | 82.9 | 0.30 | | | |
| Hydrogen Cyanide | | 100 | | | | | |
| 3-Pentenenitrile | | | | 19.5 | 61.6 | 8 | 8.35 |
| 4-Pentenenitrile | | | | — | 1.4 | — | |
| 2-Methyl-3-Butenenitrile | | | | 9.45 | 35.3 | 2.2 | |
| 2-Pentenenitrile | | | | — | 0.7 | | 2.0 |
| Cyclohexane | | | | — | | | 3.25 |
| Adiponitrile | | | | 5.12 | | 6.5 | 6.25 |
| Methylglutaronitrile | | | | 2.72 | | 3.5 | 2.00 |
| Tritolylphosphite | | | | 51.44 | | 68.7 | 69.8 |
| Cresol | | | | 1.44 | | 1.3 | 0.6 |
| Zerovalent Nickel (as Ni°) | | | | 0.40 | | 0.52 | 0.94 |

*Except for Ni and materials to be separated, compounds present at a level less than about 0.5% are not noted.

I claim:

1. A process for separating alkenes from a mixture comprising alkenes and alkadienes which process comprises contacting the mixture with hydrogen cyanide in the presence of a zero-valent nickel complex as a catalyst under hydrocyanation conditions at a temperature in the range 40°–200° C. and at a pressure in the range 0.1 –5 MPa in the liquid phase, whereby the hydrogen cyanide reacts with at least a portion of the alkadiene present to form the corresponding nitrile and thereafter separating the unreacted alkenes from the nitrile reaction product.

2. The process of claim 1 wherein the alkene has 2–5 carbon atoms and the alkadiene has 3–8 carbon atoms.

3. The process of claim 2 wherein the hydrocyanation is conducted in the presence of a zerovalent nickel catalyst having the formula $NiL_4$ wherein L is $P(OAr)_3$ and Ar is a group selected from alkyl and aryl groups having 6–10 carbon atoms.

4. The process of claim 1 wherein the hydrocyanation is conducted in the presence of a zerovalent nickel catalyst having the formula $NiL_4$ wherein L is $P(OAr)_3$ and Ar is a group selected from alkyl and aryl groups having 6–10 carbon atoms.

5. The process of claim 3 wherein the molar ratio of ligand, L, to nickel is in the range 2–26.

6. The process of claim 4 wherein the molar ratio of ligand, L, to nickel is in the range 2–26.

* * * * *